United States Patent [19]

Bontemps

[11] Patent Number: 4,681,095

[45] Date of Patent: Jul. 21, 1987

[54] PORTABLE DEVICE FOR SKIN MASSAGE BY COLD

[76] Inventor: Raymond Bontemps, 5 Rue Edouard DeVaille, Paris, France

[21] Appl. No.: 873,833

[22] Filed: Jun. 9, 1986

Related U.S. Application Data

[63] Continuation of Ser. No. 681,235, Dec. 13, 1984, abandoned.

[30] Foreign Application Priority Data

Dec. 19, 1983 [FR] France .................. 83 20273

[51] Int. Cl.⁴ ............................................. A61H 7/00
[52] U.S. Cl. ...................................... 128/24.1; 128/67
[58] Field of Search .............. 128/24.1, DIG. 27, 67, 128/62 R; 215/12 A

[56] References Cited

U.S. PATENT DOCUMENTS

| Re. 19,520 | 4/1935 | Dykema | 604/295 |
|---|---|---|---|
| 874,251 | 12/1907 | Schelling | 128/62 R |
| 1,497,764 | 6/1924 | Simonson et al. | 215/12 A |
| 1,725,530 | 8/1929 | Krauter | 128/62 R |
| 1,744,423 | 1/1930 | Toadrine | 128/24.1 |
| 1,769,872 | 7/1930 | Weeks | 128/24.1 |
| 1,833,105 | 11/1931 | Aronson | 128/62 R |
| 2,650,587 | 9/1953 | Borcovec | 128/24.1 |
| 2,706,571 | 4/1955 | Ryan | 215/12 R |
| 2,745,569 | 5/1956 | Seaman | 215/12 R |
| 2,837,128 | 6/1958 | Marchant | 604/295 |
| 2,854,003 | 9/1958 | Kirsch | 604/295 |
| 3,168,895 | 2/1965 | Okuhara | 128/24.1 |
| 3,461,728 | 8/1969 | Paoli | 73/426 |
| 4,520,799 | 4/1985 | Kruger | 128/67 |

FOREIGN PATENT DOCUMENTS

| 607367 | 3/1926 | France | 604/291 |
|---|---|---|---|
| 299913 | 11/1928 | United Kingdom | 128/62 R |
| 798058 | 7/1958 | United Kingdom | 604/295 |

Primary Examiner—Edgar S. Burr
Assistant Examiner—Tonya Lamb
Attorney, Agent, or Firm—Kramer and Brufsky

[57] ABSTRACT

This invention relates to a portable cold device for skin massage through the vasodilatation effect that follows the vasoconstrictor effect of cold. A small ball that contains glycerine and pure alcohol, preserved at −20° C., is closed by means of a rubber or plastic teat that has an application device or tip. A neck of the ball has an insulating collarette to make it easy to hold and manipulate.

5 Claims, 3 Drawing Figures

PORTABLE DEVICE FOR SKIN MASSAGE BY COLD

This application is a continuation of application Ser. No. 681,235, filed Dec. 13, 1984, now abandoned.

This invention relates to a nonmetallic container, preferably made of glass and ball-shaped with an easy-carry neck. This closed container contains either glycerine and alcohol or pure alcohol and can be maintained at −20° C. in a freezer and is used to apply cold for skin treatment and can also be used for local anesthetization.

It is known that a cold device (−10° C. to −20° C.) applied to the skin provides a local vasoconstrictor effect, so impurities in the pores are eliminated. Local warm-up follows because of activation of blood circulation. The stronger the vasoconstriction is, the more intense the vasodilatation is. The alternating vasoconstriction/vasodilatation makes the skin softer and permits the skin to be more receptive to any cosmetic product.

Given these parameters, a device is proposed that could provoke a skin vasoconstriction in order to ameliorate the absorption of a substance during the vasodilatation. Such a device could also make the skin softer by means of a massage.

Up to now, several ways were used to make the skin soft and to ameliorate the absorption of a substance. These included skin cleaning (with soap), then dry cleaning and manual massage. However, these operations had many drawbacks like:

The use of chemical products that could spoil the skin if treatments were frequent.

A long treatment that needs several hours and that could only be performed in special rooms where there is necessary instrumentation.

An expensive cost because of use of expensive chemical products.

It is to avoid these drawbacks that it is here proposed a portable device for skin massage by cold.

This portable device is characterized in that it is constituted of a small ball containing glycerine and alcohol or pure alcohol. This ball is closed by means of a flexible teat that is on the upper part of the ball neck. The lower part of the ball neck is linked to the teat. The neck of the ball has a collar of rubber or any insulating substance to carry and hold the device easily. This device is maintained in a freezer at −20° C. until use.

This invention has many advantages and particularly:

It is easy to use by anyone that wishes to receive a local skin massage, anywhere, without any chemical product.

It is cheap to use.

The device can be used for local anesthetization in order to avoid any anesthetic.

It is easy to apply on any part of the body, even the more difficult to treat.

This invention will be better understood by means of drawings that are presented as examples:

Figure 1:
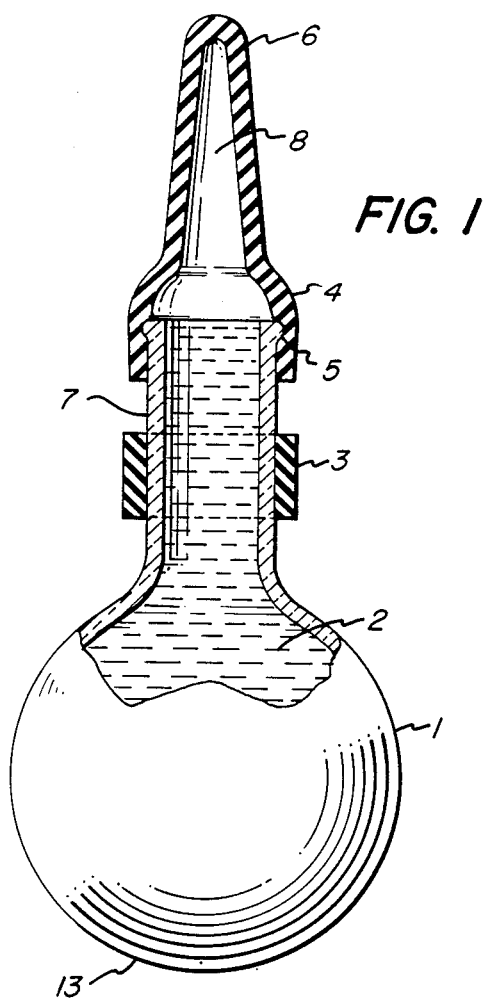
FIG. 1 illustrates a cross-sectional view of the device of the invention.

Referring to FIG. 1, the device is shown according to a sectional view. This device is constituted by a 50 cm³ ball that contains either alcohol and glycerine or pure alcohol (2). The ball (1) has a round lower part (13) to make it easy to apply to the skin. The upper part of the ball has a neck (7) in order to carry and hold the device. To carry and hold it easily, the neck (7) has a rubber collarette (3) or one made of any insulating material. The ball (1) is closed at its upper part by a rubber teat (4). At the lip (5), this teat is pear-shaped whose end is a hollow channel (8) with a pointed tip (6). The teat is placed in order to use the tip (6) as the local massage operator.

Figure 2:
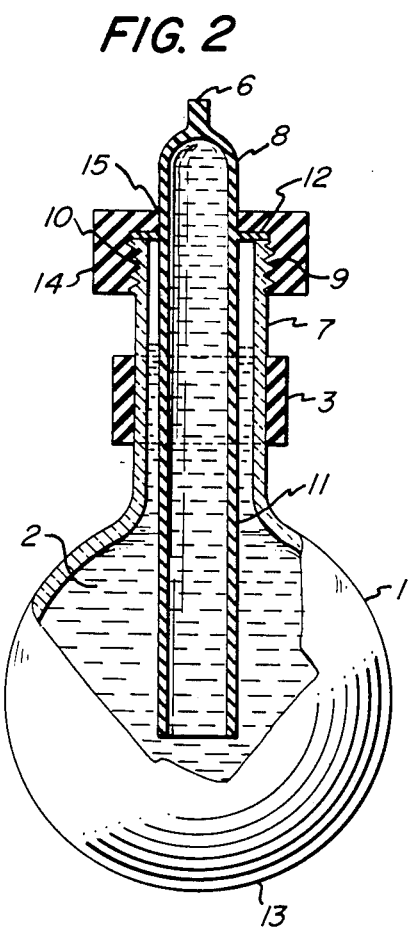
FIG. 2 illustrates a cross-sectional view of another form of the invention, with a screw teat.

According to another form of the invention in FIG. 2, the same device is shown with a screw stopper (14) and a teat (6) full of cold liquid whatever the position of the device is during operation. The device is composed of a glass ball (1) whose lower part is round (13) and the upper part has a neck (7) with a glass molded thread (10). The ball (1) is filled with either alcohol and glycerine or with pure alcohol (2). The neck of the ball (7) is closed by a screw plastic stopper (14) whose threads (9) are complemental to the ball neck (7) threads (10). The plastic stopper (14) has, at its upper part a hole (15) for receiving the teat (8). This teat has a tip (6) used as the massage component and its lower part is a hollow shank (11) that goes in the liquid (2) of the ball (1). The teat (8) and the hollow shank (11) are made of the same material (flexible plastic or rubber) and are formed integral with a flange seated on the top of the neck (7) to keep the plastic screw stopper (14) sealed. To carry and hold the device easily, the neck of the ball (7) has a rubber collarette (3) or one made of any insulating plastic.

Figure 3:
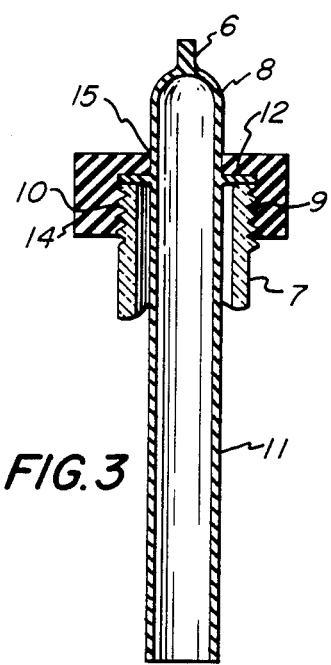
FIG. 3 illustrates the teat and the screw stopper to maintain the teat full of cold liquid regardless of the position the device has during operation.

FIG. 3 illustrates the teat (8) components of the device described in FIG. 2. The closed tip (6) placed on the upper part of the teat (8) has a tight seal at the flange (12) and a hollow shank (11). The whole is molded from a plastic material that has physical characteristics of rubber. This teat and its components go into the hole (15) on the threaded stopper (14) in sealing engagement.

USE

The ball (1) is full of either alcohol and glycerine or pure alcohol near the upper level of the neck (7). In the embodiment of FIG. 2, the ball receives the teat (8) composed of the tight flange seal (12) and the hollow shank (11) that goes into the liquid (2). The whole becomes tight with the threaded stopper (14) screwed onto the threads (10). When these operations are finished, the air in either of the teats (8) is exhausted and is replaced by liquid from the ball by pressuring or squeezing the teat (8) to exhaust air from the teat (8) causing liquid to rise in the teat (8) to the tip (6) and remain near the tip, or by inverting the device. Then the whole is maintained a few hours at −20° C. in a freezer.

For a massage using the device of either embodiment, the ball is held with the collarette (3) and its round lower part (13) is applied on the skin with a slow and increasing massage. For a local massage, the tip (6) of the teat (8) is used and in the embodiment of FIG. 2, whatever the position of the device, the teat (8) stays full of the liquid at −10° C. or −20° C.

What is claimed is:

1. A skin massager comprising:
   a glass flask having upper and lower integral portions, said lower portion being substantially spherical and terminating in an upper portion said upper portion being cylindrical; said flask being substantially completely filled with a liquid capable of being maintained as a liquid at −20° C.;

an annular insulating collar coaxially disposed about a portion of said upper portion; and closure means including a flexible teat affixed to said upper portion;

said teat being completely filled with said liquid during use and having a soft tip for massaging the skin.

2. A device in accordance with claim 1, wherein the liquid is an alcohol or a mixture of alcohols.

3. A device in accordance with claim 1 wherein said collar is made of rubber.

4. A device in accordance with claim 1 wherein said teat is formed integrally with a hollow shank received in said liquid and which is adapted to cooperate with a stopper threadedly connected to said upper portion to form the closure means for said device.

5. A device in accordance with claim 4 wherein said teat is provided with a flange seated on the top of said upper portion to seal the interior of said device.

* * * * *